United States Patent [19]

Rutledge et al.

[11] Patent Number: 4,976,062

[45] Date of Patent: Dec. 11, 1990

[54] RODENT OR REPTILE REPELLING PRODUCT AND METHOD

[76] Inventors: Justin Rutledge, 3 Lakeside La.; Steven Rutledge, 509 Holden, both of Newport, Ark. 72112

[21] Appl. No.: 202,326

[22] Filed: Jun. 2, 1988

[51] Int. Cl.$^5$ .................................................. A01M 13/00
[52] U.S. Cl. ........................................... 43/131; 43/125
[58] Field of Search ................................... 43/131, 125

[56] References Cited

U.S. PATENT DOCUMENTS

| Re. 32,513 | 10/1987 | Seaber et al. | |
|---|---|---|---|
| 1,611,119 | 12/1926 | Lipper. | |
| 1,989,427 | 1/1935 | Robey. | |
| 2,606,065 | 8/1952 | Logan et al. | 43/131 |
| 2,613,991 | 10/1952 | Schindler. | |
| 2,790,744 | 4/1957 | Shearer et al. | |
| 3,032,915 | 5/1962 | Giroud-Abel | 43/131 |
| 3,574,150 | 4/1971 | Jefferson et al. | 43/131 |
| 3,719,751 | 3/1973 | Rauscher et al. | 43/131 |
| 3,771,254 | 11/1973 | Scott et al. | 43/131 |
| 4,158,440 | 6/1979 | Sullivan et al. | |
| 4,215,508 | 8/1980 | Allen et al. | 43/131 |
| 4,275,835 | 6/1981 | Miksic et al. | |
| 4,597,218 | 7/1986 | Friemel et al. | 43/131 |
| 4,600,146 | 7/1986 | Ohno. | |

*Primary Examiner*—Richard K. Seidel
*Attorney, Agent, or Firm*—Wood, Phillips, Mason, Recktenwald & Van Santen

[57] ABSTRACT

A chemical barrier for rodents and/or reptiles including an elongated flexible, porous fabric tube 22 of a generally rope-like size, shape and flexibility contains a plurality of elongated bodies, 24, 26 ... of granular repellent material 28. The bodies 24, 26 ... are spaced from each other by short, generally repellent free gaps 30 within the tube 22 and the size of the granules 28 in each body is sufficiently large that they cannot pass through the fabric forming the tube 22. Barriers 32 at the gaps 30 prevent the entry of the repellent material 28 into the gaps and allow the tube 22 to be severed in the gaps 30 within spillage of repellent material 28.

5 Claims, 1 Drawing Sheet

4,976,062

RODENT OR REPTILE REPELLING PRODUCT AND METHOD

FIELD OF THE INVENTION

This invention relates to a simple and economical product that may be utilized to protect areas, such as food storage areas or gardens, from animals, most notably rodents and/or reptiles, and to a method of protecting such areas.

BACKGROUND OF THE INVENTION

For an untold number of years, protecting foodstuffs from animals such as rodents has been a problem. Traps, poisoned baits, physical barriers and even chemical barriers of all sorts have been utilized. The precise form in which they have been utilized depends, of course, upon the particular environment in which the foodstuffs to be protected is located.

One commonly used approach of a gardener desiring to keep, for example, rabbits out of a vegetable or flower garden is to erect a chemical barrier about the periphery of the garden. Not untypically, the chemical barrier would be made up of common mothballs set in the soil about the periphery of the garden. The vapors given off by the mothballs are apparently quite repulsive to rabbits and other rodents as well as to reptiles and thus serve as an excellent chemical barrier repelling their entry into the protected area.

A couple of difficulties attend the use of this type of barrier. For one, human traffic into and out of the garden may result in the continuity of the barrier being broken. For example, several adjacent mothballs might be kicked to one side by a person entering or leaving the protected area, thereby leaving a gap in the barrier through which rodents and/or reptiles might enter.

Secondly, this sort of chemical approach is not readily usable indoors because the unconstrained mothballs are, in a word, messy.

The present invention is directed to overcoming one or more of the above problems.

SUMMARY OF THE INVENTION

It is a principal object of the invention to provide a new and improved chemical barrier for repelling rodents and/or reptiles. More specifically, it is an object of the invention to provide such a barrier which is not easily disturbed and which may be readily used indoors if desired.

An exemplary embodiment of the invention achieves the foregoing object in a rodent and/or reptile repellent product including an elongated tube of flexible material. The wall of the tube is porous. A body of granular repellent material is located within the tube and is distributed along the length thereof. The granules of the repellant material are sufficiently large that they will not freely pass through the tube wall.

According to a preferred embodiment of the invention, the flexible material is a fabric.

In a highly preferred embodiment, the repellent material is distributed along the length of the tube in alternating, relatively long sections of repellent material and relatively short sections that are free of repellent material. The barriers close both ends of the relatively long sections to prevent the repellent material from exiting the relatively long sections while allowing the device to be sized without spillage of the repellent material by severing the tube at selected ones of the relatively short sections.

In a highly preferred embodiment, the barriers are formed by lines of stitches extending across the tube and delineating the relatively long sections from the relatively short sections.

Generally, the tube will have a uniform cross section along its length and will be generally of a rope-like size and shape and flexibility.

Preferably, the tube is formed of a fabric made of a spun polymer material for economy.

The invention contemplates a method of protecting an area from rodents and/or reptiles which includes the steps of sizing a repellent product such as mentioned immediately preceding to extend about the periphery of the area to be protected by severing the product at one or more of the gaps between the repellent material bodies to provide a section of the device having a length equal to or greater than the periphery and thereafter locating the section resulting from the performance of the severing step in a closed loop about the periphery of the area to be protected.

As a result of the foregoing, a chemical barrier that is not easily dislodged is provided. Furthermore, because the chemical material is contained within the tube, and in the most preferred embodiments, retained therein by barriers, the chemical materials cannot come free of the tube permitting the use of the barrier indoors without creating a mess. Even the severing of the tube when sized using the gaps between adjacent bodies of repellent material will not result in spillage of the repellent material.

Other objects and advantages will become apparent from the following specification taken in connection with accompanying drawings.

DESCRIPTION OF THE PREFERRED EMBODIMENT

Figure 1:
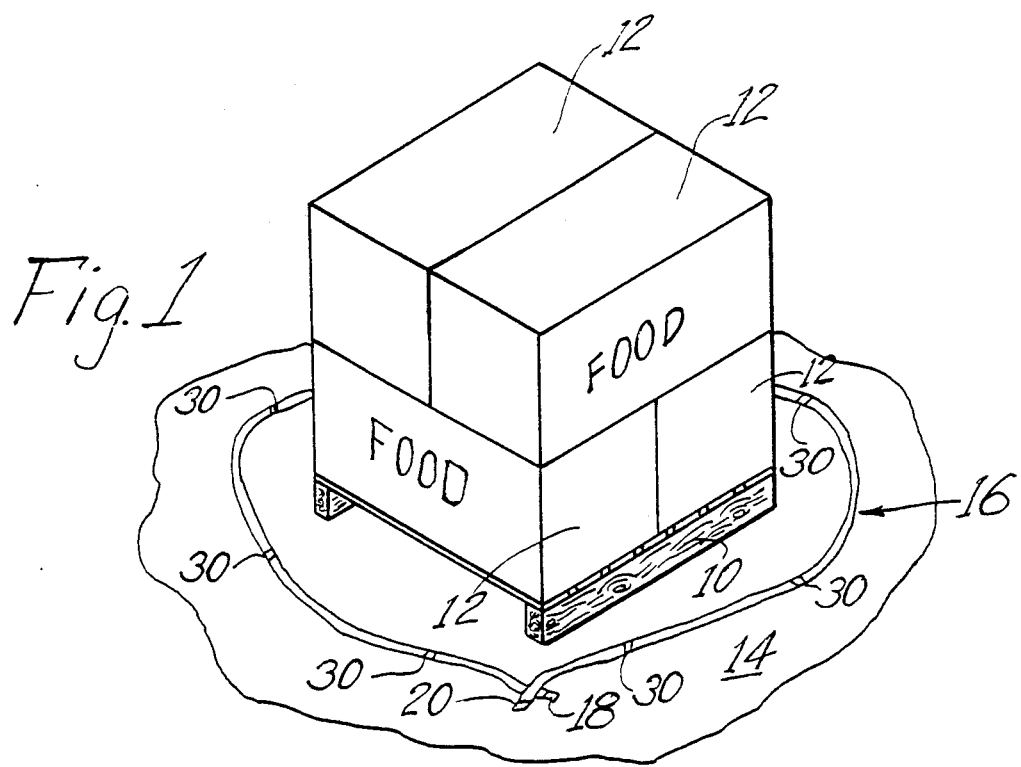
FIG. 1 is a perspective view of a rodent and/or repellent product being utilized to protect an area containing foodstuffs.

An exemplary embodiment of a repellent product made according to the invention is illustrated in the drawings and with reference to FIG. 1 is seen in a typical indoor use. A conventional wooden pallet 10 is supporting a plurality of food containers 12 above the floor 14 of, for example, a warehouse. The pallet 10 thus constitutes the area to be protected.

According to the invention, the repellent product, generally designated 16, is disposed about the pallet 10 in a closed loop. Opposite ends 18 and 20 of the repelling device may simply be overlapped as illustrated in FIG. 1 or they may simply be brought into close adjacency. Alternatively, they could be tied together if desired.

The repellent product 16 provides a functionally continuous chemical barrier about the area to be protected when oriented as illustrated in FIG. 1. However, in a preferred embodiment, the chemical barrier, while being functionally continuous, is not physically continuous.

In particular, the repelling device is preferably made up of a fabric tube 22 which is flexible and porous. Typically, the tube will be on the order of ⅓ to 1 inch in diameter so as to be somewhat rope-like in size, shape and flexibility.

Figure 2:
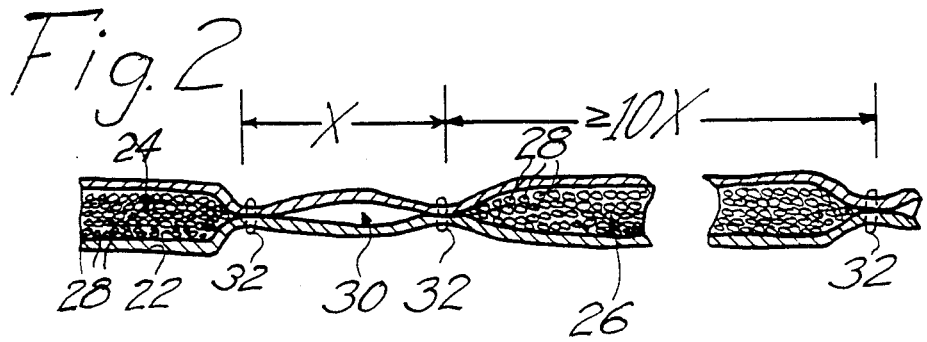
FIG. 2 is a fragmentary, sectional view of the repelling device.

Within the tube 22 there is located a plurality of bodies of repellent material. In FIG. 2, one such body is partially illustrated at 24 while an adjacent such body is illustrated at 26. Each body 24, 26, etc. is in turn made up of granules 28 of the repellent material. According to the invention, the granules 28 may be conventional moth flakes. Flakes are preferred over moth crystals as the latter have a tendency to cut the material of which the tube 22 is formed.

The bodies 24, 26 etc. are separated by relatively small gaps 30 that are free from the granules 28. As can be ascertained from FIGS. 1 and 2, the length of each gap 30 is quite short as compared to the length of each body 24, 26 of repellent material. Illustratively, the length of a body 24, 26 of repellent material will be equal to or greater than ten times the length of a gap 30 and generally speaking, each gap 30 will have a length "X" that does not exceed one inch.

Figure 3:
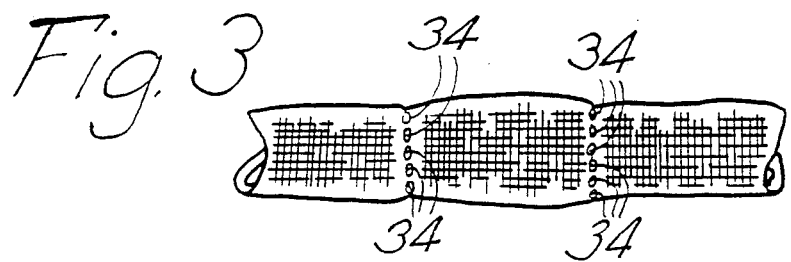
FIG. 3 is a fragmentary, plan view of the repelling device.

The tube 22 is provided with barriers at each end of each of the bodies 24, 26. Such barriers are designated 32 and illustratively may be made up of stitches 34 (FIG. 3) extending generally transversely to the length of the tube 22. Stated another way, each gap 30 is delineated by spaced parallel rows of stitches 34. However, it is to be understood that other means of closure might be utilized. For example, if the tube 22 is made of heat sealable material, a heat seal might be used in lieu of the stitches 34. Alternatively, adhesives might be employed or even sonic welding to form suitable weld lines. In addition, rather than delineating each gap 30 by spaced parallel lines of closures as illustrated in FIGS. 2 and 3, a single closure of substantial width could be utilized. For example, a single heat seal applied across the gap 30 between the barriers 32 shown in FIG. 2 could be utilized.

In a preferred embodiment, the tube 22 is formed for a spun bonded polymer fabric as, for example, spun bonded polypropylene or spun bonded polyester. This provides a highly porous tube 22 but yet a tube whose pores are significantly smaller than the size of the granules 28 making up each of the bodies 24, 26 etc. Thus, the repelling material cannot freely pass through the walls of the tube 22 into the surrounding environment to create a messy condition and yet the vapors emitted by the material may freely exit the tube 22 to repel rodents and/or reptiles.

In the usual case, the gaps 30 will be located at, for example, one foot intervals along the length of the repelling device 16. They provide a convenient means of sizing the repelling device 16 to protect a given area. In particular, the length of the periphery of the area to be protected may be determined and an equal or greater length of the repelling device 16 cut from a supply thereof without spillage of the repelling material by severing the tube 22 at one of the gaps 30 between the barriers 32.

From the foregoing, it will be appreciated that a repellent product made according to the invention has many advantages over chemical barriers heretofore used. For example, it is easily and simply applied to an area to be protected.

It can be applied to the area to be protected without spillage of the chemical media used as a repellent and may be maintained in such use without any such spillage. Furthermore, dislodging of the chemical barrier is much more difficult. At the same time, once the need for use of the barrier is over, the same may be readily removed and disposed of as appropriate.

We claim:

1. An animal repelling product comprising:
   an elongated, flexible, porous tube of a rope-like size, shape and flexibility;
   a plurality of elongated bodies of granular repellant material disposed within said tube and spaced from each other by short generally repellent material free gaps within said tube, the size of the granules in each body being sufficiently large that they cannot pass through said tube; and
   barrier means in said gaps for preventing the entry of said repellent material into said gaps and allowing said tube to be severed in said gaps without spillage of repellent material from the tube.

2. The repelling product of claim 1 wherein the barrier means at each said gap comprises two, spaced, generally parallel closure lines extending across said tube.

3. The repelling product of claim 2 wherein said closure lines are defined by stitches.

4. The repelling product of claim 1 wherein said tube is a spun bonded polymer fabric.

5. A method of protecting an area from animals comprising the steps of:
   (a) providing an animal repelling product including an elongated, flexible, porous tube of a ropelike size, shape and flexibility;
   a plurality of elongated bodies of granular repellant material disposed within said tube and spaced from each other by short generally repellant material free gaps within said tube, the size of the granules in each body being sufficiently large that they cannot pass through said tube;
   and barrier means in said gaps for preventing the entry of said repellant material into said gaps and allowing said tube to be severed in said gaps without spillage of repellant material from the tube;
   (b) sizing said repelling product to extend about the periphery of the area to be protected by severing the same at one or more gaps to provide a section of said device having a length equal to or greater than said periphery; and
   (c) locating the section resulting from step (b) in a closed loop about the periphery of the area to be protected.

* * * * *